United States Patent [19]

Yoshikawa et al.

[11] Patent Number: 5,268,360
[45] Date of Patent: Dec. 7, 1993

[54] OPIOID PEPTIDES DERIVED FROM WHEAT PROTEINS

[75] Inventors: Masaaki Yoshikawa, Joyo; Shin-ichi Fukudome, Kyoto, both of Japan

[73] Assignee: Nisshin Flour Milling Co., Ltd., Tokyo, Japan

[21] Appl. No.: 801,388

[22] Filed: Dec. 2, 1991

[30] Foreign Application Priority Data

Dec. 27, 1990 [JP] Japan .................. 2-418333
Feb. 27, 1991 [JP] Japan .................. 3-53745
Jun. 18, 1991 [JP] Japan .................. 3-171879

[51] Int. Cl.[5] .................. A61K 37/00; C07K 5/00
[52] U.S. Cl. .................. 514/18; 514/17; 530/329; 530/330
[58] Field of Search .............. 514/17, 18; 530/329, 530/330

[56] References Cited

PUBLICATIONS

Journal of Biological Chemistry, vol. 254, No. 7, Apr. 10, 1979, pp. 2446–2449, C. Zioudrou, et al. "Opioid Peptides Derived from Food Proteins".

Peptides, vol. 5, Ankho International Inc. USA, 1984, pp. 1139–1147, F. R. Huebner, et al., "Demonstration of High Opioid–Like Activity in Isolated Peptides from Wheat Gluten Hydrolysates".

Gastroenterology, vol. 84, No. 6, American Gastroenterological Association, 1983, pp. 1517–1523, J. E. Morley, et al., "Effect of Exorphins on Gastrointestinal Function, Hormonal Release, and Appetite".

Journal of Medicinal Chemistry, vol. 21, No. 11, American Chemical Society, 1978, pp. 1110–1115, P. W. Schiller, et al. "Synthesis, Opiate Receptor Affinity, and Conformational Parameters of [4-Tryptophan]Enkephalin Analogues".

Primary Examiner—Merrell C. Cashion, Jr.
Assistant Examiner—Bennett Celsa
Attorney, Agent, or Firm—Oblon, Spivak, McClelland, Maier & Neustadt

[57] ABSTRACT

Disclosed are opioid peptides recovered from hydrolysates of wheat proteins with an acid protease and further a neutral or alkaline protease. Of those peptides, the structure of four opioid peptides was identified by the amino acid sequence of Gly-Tyr-Tyr-Pro (SEQ ID NO:1), Gly-Tyr-Tyr-Pro-Thr (SEQ ID NO:2), Gly-Tyr-Tyr-Pro-Thr-Ser (SEQ ID NO:3) or Tyr-Pro-Ile-Ser-Leu (SEQ ID NO:4). They are useful as a medicine such as narcotic, analgesic or the like.

2 Claims, 2 Drawing Sheets

OPIOID PEPTIDES DERIVED FROM WHEAT PROTEINS

FIELD OF THE INVENTION

This invention relates to new peptides having opioid activity derived from wheat proteins, in particular wheat gluten, processes for the preparation thereof and pharmaceutical compositions comprising those peptides as active ingredient.

BACKGROUND OF THE INVENTION

It is known that the peptides derived from food proteins (casein, gluten) possess opioid activities such as morphine-like narcotic, analgesic activities and may be of physiological importance.

C. Zioudrou et al have reported that peptides with opioid activity are found in pepsin hydrolysates of wheat gluten and α-casein and also the activity is demonstrated by use of the bioassays including naloxone-reversible inhibition of adenylate cyclase in homogenates of neuroblastoma X glioma hybrid cells and of electrically stimulated contractions of the mouse vas deferens (J. Biol. Chem. vol. 254, No. 7, pp. 2446–2449, 1979).

F. R. Huebner et al have recognized the opioid activities in the fragments derived from gliadin fraction by the radioreceptor assay (Peptides, vol. 5, pp. 1139–1147, 1984).

John E. Morley et al have reported that hydrolyzed gluten prolongs intestinal transit time and this effect is reversed by concomitant administration of naloxone and also that hydrolyzed gluten produces a naloxone-reversible increase in plasma somatostatinlike activity, which may have been responsible for the delayed transit time (Gastroenterology vol. 84, No. 6, pp. 1517–1523).

These reports have suggested that opioid peptides have been detected in gluten hydrolysates, but it has not as yet proven possible to elucidate the structure and character of those peptides.

We recognized that the active peptides could not isolated from pepsin hydrolyzates of wheat gluten because of its very weak activity. The present invention results from our continuing efforts to isolate new opioid peptides with the specified structures from the gluten hydrolysates.

SUMMARY OF THE INVENTION

It is therefore an object of the present invention to provide new opioid peptides having the specified amino acid sequence isolated from the hydrolysates of wheat proteins.

It is further object of the invention to provide processes of preparing opioid peptides by enzymatic hydrolysis or chemical synthesis.

It is another object of the invention to provide pharmaceutical compositions comprising the opioid peptides as active ingredient.

DETAILED DESCRIPTION OF THE INVENTION

The present invention provides peptides having opioid activity (opioid peptides) which are prepared from a hydrolysis of wheat proteins by proteases. The opioid peptides of the invention contain those with the determined structure and those with the undetermined structure, both of which are included within the scope of the invention. Among peptides of the invention, those with the determined structure can include opioid peptides, each having the following amino acid sequence:

| | |
|---|---|
| Gly-Tyr-Tyr-Pro (SEQ ID NO:1) | (1) |
| Gly-Tyr-Tyr-Pro-Thr (SEQ ID NO:2) | (2) |
| Gly-Tyr-Tyr-Pro-Thr-Ser (SEQ ID NO:3) | (3) |
| Tyr-Pro-Ile-Ser-Leu (SEQ ID NO:4) | (4) |

Four opioid peptides having the sequences (1) (2) (3) and (4), respectively (SEQ ID NO:1), (SEQ ID NO:2), (SEQ ID NO:3) and (SEQ ID NO:4) are new and called herein for convenience "Peptide A", "Peptide B", "Peptide C" and "Peptide D", respectively. So far as we are aware, there is no report on the preparation and isolation of four peptides from wheat proteins by enzymatic hydrolysis or chemical synthesis.

Among peptides of the invention, opioid peptides each having the following amino acid sequence

| | |
|---|---|
| Tyr-Gly-Gly-Trp-Leu (SEQ ID NO:5) | (5) |
| Tyr-Gly-Gly-Trp (SEQ ID NO:6) | (6) | are known by J. Med. Chem. 1978, vol. 21, No. 11, pp. 1110–1115, but there is no report on the preparation and isolation of two peptides from wheat proteins by enzymatic hydrolysis. Two opioid peptides having the sequences (5) and (6), respectively (SEQ ID NO:5) and (SEQ ID NO:6) are called herein for convenience "Peptide E" and "Peptide F", respectively. The amino acids constituting the opioid peptides of the invention may be in any of D-, L- and DL-configurations.

The peptides of the present invention can be prepared by new enzymatic process which comprises hydrolysis of wheat proteins by an acid protease, further hydrolysis of the hydrolysates by a neutral protease or an alkaline protease and optionally fractionation, isolation and purification of the resultant peptide mixture by conventional means. The amino acid sequence of the peptides thus isolated may be decided for example by use of a protein sequencer.

Based on the amino acid sequence as decided, the peptides of the present invention can also be synthesized by a conventional method, e.g. a solid-phase synthesis according to the t-Boc strategy.

The wheat proteins which are usable in the invention can include gluten alone and a mixture of gluten with other proteins in wheat such as albumin, gliadin, globulin.

The acid proteases which are usable in the invention can include pepsin and aspartic proteinases derived from *Pycnoporus coccineus*, *Aspergillus* and *Penicillium*. They may be used alone or in combination therewith so long as it is not adversely affected each other. If a plurality of acid proteases are used, hydrolysis may be performed with simultaneous use of varying proteases or successive use of each protease.

The neutral proteases which are usable in the invention can include metal proteases derived from microorganisms including heat resistant proteases from Bacillus such as thermolysin, those derived from Aspergillus, Streptomyces and Rhizopus; those derived from plants such as papain, bromelain; and those existing in vivo of animals such as trypsin, chymotrypsin, plasmin and thrombin.

The alkaline proteases which are usable in the invention can include cerin proteases derived from Bacillus or the like.

The neutral or alkaline protease may be used alone or in combination therewith so long as it is not adversely affected each other. If a plurality of neutral proteases are used, hydrolysis may be performed with simultaneous use of varying proteases or successive use of each protease.

Fractionation, isolation and purification can be performed by known means such as membrane separation and chromatographic process. In the process of the invention, preferred is a high performance liquid chromatography (HPLC) including reversed-phase chromatography (RPC) on an octadecyl silane (ODS) column, a phenyl column, a cyanopropyl column and a phenetyl column.

The peptides of the invention possess opioid activities which are involved in analgesic, narcotic, affection, respiration, pulsation, body temperature, gastrointestinal function, athrocytosis, immunity, regulation of hormone secretion such as insulin and somatostatin, enhanced absorption of electrolyte and regulated contraction of myocardium, which may be useful as an analgesic and narcotic agent, a hypnotic agent, a secretion enhancer of gastrointestinal hormone, an absorption enhancer of electrolyte or the like. Thus the present invention also provides pharmaceutical compositions comprising as active ingredient opioid peptides each having the amino acid sequence of formulas (1) to (6) or physiologically acceptable salts thereof. The opioid peptides or their salts of the invention, because of being a water soluble white powder can be administered orally or parenterally as they are or in the form dissolved in water. Depending on the mode of administration, the opioid peptide may be formulated with a wide variety of physiologically acceptable carriers. The dosage forms may include tablets, capsules, suppositories, troches, syrups, granules, powders, injectable solutions or suspensions. An appropriate dose can be chosen depending on the dosage form, age and sex of patients, degree of symptom, etc.

The opioid peptides of the invention can be added to foods and feeds.

PREFERRED EMBODIMENTS OF THE INVENTION

Hydrolysis of Wheat Gluten

Wheat gluten is hydrolyzed with proteases to prepare a water-soluble peptide mixture. Initially, wheat gluten is hydrolyzed with an acid protease in such a situation that it is dispersed and dissolved in an acid solution such as diluted hydrochloric acid. Subsequently, the hydrolysate is neutralized or made alkaline and further hydrolyzed with a neutral or alkaline protease to prepare a peptide mixture. In that case, the peptide mixture containing Peptides A (SEQ ID NO:1), B (SEQ ID NO:2), E (SEQ ID NO:5) and F (SEQ ID NO:6) can be obtained by use of the neutral or alkaline protease. The peptide mixture containing Peptide D (SEQ ID NO:4) can be obtained by using as the neutral protease those existing in vivo of animals such as trypsin, chymotrypsin or the like. In this case, trypsin and chymotrypsin may be applied simultaneously or successively.

In the preparation of the peptides, pepsin is preferably used as the acid protease, since the desired product can be obtained in high yield.

In the preparation of Peptides A (SEQ ID NO:1), B (SEQ ID NO:2), E (SEQ ID NO:5) and F (SEQ ID NO:6), thermolysin derived from Bacillus or those derived from *Aspergillus* (especially, *Aspergillus oryzae*) are preferably used as the neutral proteases, since the desired product can be obtained in high yield.

Acid, neutral and alkaline proteases may be used in the free or immobilized state. The amount of protease used may be in the range of about 5,000 to 100,000 units per 100 g of dry gluten. The activity (unit) of protease used is assayed by Casein-Folin coloration A method described in S. Akabori, "Method of Studying Enzymes", vol. 2, p. 238, 1961 using as a substrate 1% Hamerstein casein solution available from American Merk Co. The reaction is conducted at 30° C. for 30 min. The amount of enzyme required for liberating 1 μg of tyrosin for one minute is expressed as 1 unit.

A protease treatment is advantageously performed under optimum conditions of pH, temperature, amount of protease, rate and time of treatment which are chosen according to situations such as kinds and use forms of protease, etc. In performing the hydrolysis of gluten with pepsin and then themolysin or with pepsin and then trypsin-chymotrypsin, for example, an aqueous solution or aqueous dispersion of gluten is adjusted to the pH between about 1.5 and 5.0 and hydrolyzed with pepsin at a temperature of about 30° to 50° C. Subsequently, the solution is adjusted to the pH between about 6.0 and 8.0 and further hydrolyzed with thermolysin or trypsin-chymotrypsin at a temperature of about 30° to 50° C. until a solubility in 0.75 M trichloroacetic acid is in the range of about 40 to 80%.

At the time when the hydrolysis is achieved to a desired level, proteases are deactivated by heating and/or adjustment of pH. The deactivated enzyme and any insoluble solid materials such as unhydrolyzed gluten are separated and removed by suitable means such as centrifugation to recover a peptide mixture from the residual solution by drying or the like.

Then the peptide mixture dissolved in water is subjected to HPLC, e.g., HPLC on a reversed column to isolate the desired peptide in a pure form.

Isolation of opioid peptides from the peptide mixture can be accomplished in the following manner.

Isolation of Peptides A, B, E and F ($a_1$) The peptide mixture prepared by hydrolysis of wheat gluten with pepsin and then thermolysin is subjected to HPLC on an octadecyl silane (ODS) column (e.g., Cosmosil 5 $C_{18}$-AR, Nacalai Tesque Inc.) and eluted with an aqueous 0.05% trifluoroacetic acid (TFA) solution (solution A) and an acetonitrile (ACN) solution containing 0.05% TFA (solution B) with a linear gradient between 0 to 40% the solution B. A peak fraction (fraction I) eluting in the ACN concentration between about 22.5% and 23.5%, a peak fraction (fraction II) eluting between about 24% and 25%, a peak fraction (fraction III) eluting between about 28% and 29% and a peak fraction (fraction IV) eluting between about 34% and 35% are fractionated respectively and those fractions are determined for opioid activity.

(b₁) The opioid active fractions prepared in step (a₁) are subjected to reversed-phase chromatography (RPC) on a column with different characteristics from one used in (a₁) (e.g., Cosmosil 5 Ph, Nacalai Tesque Inc.) and eluted in a similar manner as in step (a₁). A peak fraction (fraction I-1) eluting in the ACN concentration between about 24% and 25% is separated from fraction I, a peak fraction (fraction II-1) eluting between about 33% and 34% is separated from fraction II, a peak fraction (fraction III-1) eluting between about 30% and 31% is separated from fraction III and a peak fraction (fraction IV-1) eluting between about 36% and 37% is separated from fraction IV. Those fractions are determined for opioid activity.

(c₁) The opioid active fractions prepared in step (b₁) are subjected to reversed-phase chromatography (RPC) on a column with different characteristics from one used in (b₁) (e.g., Cosmosil 5 CN R, Nacalai Tesque Inc.) and eluted in a similar manner as in steps (a₁) and (b₁). A peak fraction (fraction I-2) eluting in the ACN concentration between about 18% and 19% is separated from fraction I-1, a peak fraction (fraction II 2) eluting in the ACN concentration of about 27% is separated from fraction II-1, a peak fraction (fraction III-2) eluting between about 26% and 27% is separated from fraction III-1 and a peak fraction (fraction IV-2) eluting between about 32% and 33% is separated from fraction IV-1. Those fractions are determined for opioid activity.

(d₁) Of the opioid active fractions prepared in step (c₁), fractions I-2, III-2 and IV-2 are subjected to the column used in (a₁) and then eluted with 10 mM $KH_2PO_4$—$Na_2HPO_4$ buffer (pH 7) (solution C) and 50% ACN solution containing 10 mM $KH_2PO_4$—$Na_2HPO_4$ buffer (pH 7) (solution D) with a linear gradient between 0% and 100% the solution D. A peak fraction (fraction I-3) eluting in the ACN concentration of about 18% is separated from fraction I-2, a peak fraction (fraction III-3) eluting at about 21% is separated from fraction III-2 and a peak fraction (fraction IV-3) eluting at about 28% is separated from fraction IV-2. Those fractions are determined for opioid activity.

(e₁) Of the opioid active fractions prepared in step (d₁). fraction IV-3 is subjected to the column used in (a₁) and then eluted by a similar procedure as in steps (a₁). (b₁) and (c₁). A peak fraction (fraction IV-4) eluting in the ACN concentration of about 31% is separated from fraction IV-3 which is determined for opioid activity.

(f₁) Of the opioid active fractions prepared in step (e₁), fraction IV-4 is subjected to reversed phase chromatography on a column with different characteristics from one used steps (a₁), (b₁) and (c₁) (e.g., Develosil PhA-5, Nomura Chemical Inc.) and then eluted in a similar manner as in step (d₁). A peak fraction (fraction IV-5) eluting in the ACN concentration of about 29% is separated from fraction IV-4 which is determined for opioid activity.

(g₁) Solvents are removed by drying from the opioid active fraction (fraction II-2) obtained in step (c₁). the opioid active fractions (fraction I 3, fraction III-3) obtained in step (d₁) and the opioid active fraction (IV-5) obtained in step (f₁) for recovery.

(h₁) The amino acid sequence of the dried materials obtained in step (g₁) is analyzed by a protein sequencer (e.g., 477 A protein sequencer, Applied Biosystems Inc.). Fraction I 3 was identified as Peptide B (SEQ ID NO:2), Gly-Tyr-Tyr-Pro-Thr, fraction II-2 as Peptide A (SEQ ID NO:1), Gly-Tyr-Tyr-Pro, fraction III-3 as Peptide F (SEQ ID NO:6), Tyr-Gly-Gly Trp and fraction IV-5 as Peptide E (SEQ ID NO:5), Tyr-Gly-Gly-Trp-Leu.

Isolation of Peptide D (a₂) The peptide mixture prepared by hydrolysis of wheat gluten with pepsin and then trypsin-chymotrypsin is subjected to HPLC on an octadecyl silane (ODS) column (e.g., Cosmosil 5 $C_{18}$-AR, Nacalai Tesque Inc.) and eluted with an aqueous 0.05% trifluoroacetic acid (TFA) solution (solution A) and an acetonitrile (ACN) solution containing 0.05% TFA (solution B) with a linear gradient between 0 to 40% solution B. A peak fraction (fraction V) eluting in the AC concentration between about 31% and 32% is separated to identify the opioid activity.

(b₂) The opioid active fraction (fraction V) prepared in step (a₂) is subjected to reversed-phase chromatography (RPC) on a column with different characteristics from one used in (a₂) (e.g., Cosmosil 5 Ph, Nacalai Tesque Inc.) and eluted in a similar manner as in step (a₂). A peak fraction (fraction V-1) eluting in the ACN concentration of about 33% is separated to identify the opioid activity.

(c₂) The opioid active fraction (fraction V-1) prepared in step (b₂) are subjected to reversed-phase chromatography (RPC) on a column with different characteristics from one used in steps (a₂) and (b₂) (e.g., Cosmosil 5 CN-R, Nacalai Tesque Inc.) and eluted in a similar manner as in steps (a₂) and (b₂). A peak fraction (fraction V-2) eluting in the ACN concentration between about 27% and 28% is separated to identify the opioid activity.

(d₂) The opioid active fraction (fraction V-2) prepared in step (c₂) is subjected to the column used in step (a₂) and then eluted with 10 mM $KH_2PO_4$-$Na_2HPO_4$ buffer (pH 7) (solution C) and 50% ACN solution containing 10 mM $KH_2PO_4$—$Na_2HPO_4$ buffer (pH 7) (solution D) with a linear gradient between 0% and 100% solution D. A peak fraction (fraction V-3) eluting in the ACN concentration of about 24% is separated to identify the opioid activity.

(e₂) The opioid active fraction (fraction V-3) is dried to remove the solvent and recovered.

(f₂) The amino acid sequence of the dried materials obtained in step (e₂) is analyzed by a protein sequencer (e.g., 477 A protein sequencer, Applied Biosystems Inc.). Fraction V-3 was identified as Peptide D (SEQ ID NO:4).

Alternatively, Peptides A to F (SEQ ID NOS:1-6) of the present invention can be prepared by chemical synthesis, e.g., by the following method.

Chemical Synthesis of Peptides

The peptide is synthesized by a Sam 2 peptide synthesizer (Biosearch Inc.) in accordance with a standard protocall of the synthesizer. A Boc(butoxycarbonyl)-Pro-resin is treated with a deblock solution containing 45% trifluoroacetic acid and then coupled with Boc-Tyr($Cl_2$-Bzl) in the presence of diisopropyl carbodiimide. After deblocking in a similar manner as mentioned above, the resin is coupled with successive, Boc Tyr(Cl₂Bzl) and Boc-Gly to obtain Boc-Gly-Tyr(Cl₂-Bzl) Tyr(Cl₂-Bzl)-Pro-resin. This peptide resin is placed in hydrogen fluoride containing 10% anisol and stirred at 0° C. for 1 hr. After hydrogen fluoride is distilled away, the residue is washed with ether and a peptide is extracted with 30% acetic acid. Purification of a crude peptide by HPLC on the ODS column gives Peptide A (SEQ ID NO:1).

Peptides B-F (SEQ ID NOS:2-6) can be also synthesized by a similar procedure as mentioned above.

The invention is further illustrated by the following non-limited examples.

EXAMPLE 1

Preparation of Peptides A, B, E and F from Wheat Gluten Hydrolysates (1) 5 g of wheat gluten dispersed and dissolved in 100 ml of 0.02 N HCl were centrifuged at 3500 G for 20 minutes to remove an insoluble material and the pH of the solution was adjusted to 2.0 with 1 N HCl. To this gluten solution were added 5000 units of pepsin (available from Sigma Chemical Co., U.S.A.) and the solution was incubated at 37° C. for 15 hrs. After completion of reaction, the pH of the solution was adjusted to 7.0 with 1 N NaOH, to which were added 5000 units of thermolysin (available from Peptide Research Institute Inc.) and the mixture was incubated at 37° C. for 4 hrs. After completion of reaction, the solution was heated at 90° C. for 20 minutes to deactivate the pepsin and thermolysin. The hydrolysate was centrifuged at 3500 G for 20 minutes to remove an insoluble matter and the resulting supernatant was lyophilized to yield about 3.5 g of a wheat gluten hydrolysate. (2) 80 mg of the wheat gluten hydrolysate was subjected to reversed-phase chromatography (RPC) on an octadecyl silane column (Cosmosil 5 C₁₈-AR, 20 mm I.D., 250 mm length, Nacalai Tesque Inc.) and then eluted with an aqueous 0.05% trifluoroacetic acid (TFA) solution (solution A) and an acetonitrile (ACN) solution containing 0.05% TFA (solution B) at a flow rate of 10 ml/min with a linear gradient from 0% to 40% solution B over a period of 40 minutes. The chromatogram at a wavelength of 230 nm is shown in FIG. 1.

Figure 1:
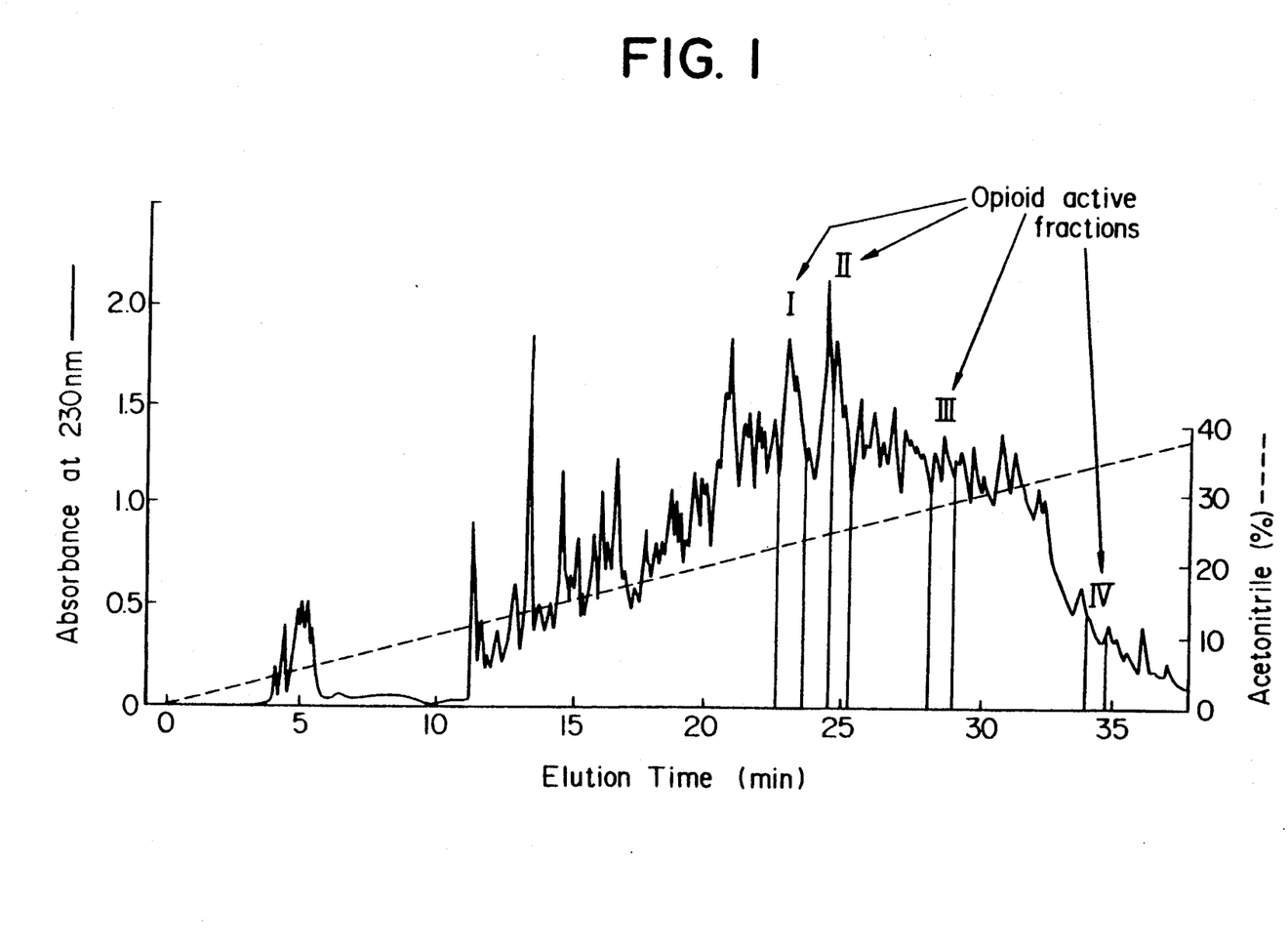
FIG. 1 shows the separation of opioid active fractions I, II, III and IV from an octadecyl silane (ODS) column.

The fractions shown in FIG. 1 was determined for opioid activity. Opioid activity was found in fraction I eluting between about 22.5 and 23.5% in the ACN concentration, fraction II eluting between about 24 and 25%, fraction III eluting between about 28 and 29% and fraction IV eluting between about 34 and 35%. (3) The same procedure as in (2) was repeated using 2000 mg of the wheat gluten hydrolysate as prepared in (1) to obtain opioid active fractions of fractions I, II, III and IV. Those active fractions were subjected to RPC using a phenyl column (Cosmosil 5 Ph, 4.6 mm I.D., 250 mm length, Nacalai Tesque Inc.) and eluted with solutions A and B at a flow rate of 1 ml/min with a linear gradient from 0% to 40% solution B over a period of 40 minutes.

Each of eluting fractions was determined for opioid activity. Opioid activity was found for fraction 1 in fraction I 1 eluting in the ACN concentration of about 24 to 25%, for fraction II in fraction II-1 eluting in the ACN concentration of about 33 to 34%, for fraction III in fraction III-1 eluting in the ACN concentration of about 30 to 31% and for fraction IV in fraction IV eluting about 36 to 37%.

(4) The opioid active fractions in fractions I-1, II-1, III-1 and IV-1 prepared in (3) were subjected to RP using a cyanopropyl column (Cosmosil 5 CN-R, 4.6 mm I.D., 250 mm length, Nacalai Tesque Inc.) and eluted under the same conditions as in (3).

Each of eluting fractions was collected and assayed for opioid activity. Opioid activity was found for fraction I-1 in a peak fraction (fraction I-2) in the ACN concentration of about 18 to 19%, for fraction II-1 in a peak fraction (fraction II-2) in the ACN concentration of about 27%, for fraction III-1 in a peak fraction (fraction III-2) in the ACN concentration of about 26 to 27% and for fraction IV in a peak fraction (fraction IV-2) in the ACN concentration of about 32 to 33%. (5) Fractions I-2, III-2 and IV-2 of the opioid active fractions as prepared in (4) above were subjected to reversed-phase chromatography (RPC) on an octadecyl silane column (Cosmosil 5 C₁₈-AR, 20 mm I.D., 250 mm length, Nacalai Tesque Inc.) and then eluted with 10 mM KH₂PO₄—Na₂HPO₄ buffer (pH 7) (solution C) and 50% ACN solution containing 10 mM KH₂PO₄—Na₂HPO₄ buffer (pH 7) (solution D) with a linear gradient from 0 to 100% solution D. Each eluting fraction was collected and assayed for opioid activity. Opioid activity was found for fraction I-2 in a peak fraction (fraction I-3) in the ACN concentration of about 18%, for fraction III-2 in a peak fraction (fraction III-3) in the ACN concentration of about 21% and for fraction IV-2 in a peak fraction (fraction IV-3) in the ACN concentration of about 28%.

(6) Fraction IV-3 of the opioid active fractions as prepared in (5) was again subjected to RPC using the same column as in (5) and eluted under the same conditions as in (4). Each eluting fraction was collected and assayed for opioid activity. Opioid activity was found in a peak fraction (fraction Iv-4) in the ACN concentration of about 31%.

(7) Fraction IV-4 of the opioid active fraction prepared in (6) was further subjected to a phenetyl column (Develosil PhA-T-5, 4.6 mm I.D., 250 mm length, Nomura Chemical Inc.) and eluted under the same conditions as in (5). The determination of each eluting fraction for opioid activity indicates that opioid activity was found in a peak fraction (fraction IV-5) in the ACN concentration of about 29%.

(8) Fraction II-2 obtained in (4), fractions I-3 and III-3 obtained in (5) and fraction IV-5 obtained in (7) were recovered, concentrated and dried.

The dried materials as prepared above were analyzed for the amino acid sequence using a 477 A protein sequencer (Applied Biosystems Inc.). For the dried material of fraction I 3, L Gly, L-Tyr, L-Tyr, L-Pro and L-Thr were successively liberated from the N terminus, which was identified as "Peptide B" having the amino acid sequence of Gly-Tyr-Tyr-Pro-Thr, all of the constituent amino acids being L-amino acids.

For the dried material of fraction II-2, L-Gly, L-Tyr, L-Tyr and L-Pro were successively liberated from the N terminus, which was identified as Peptide A (SEQ ID NO:1) having the amino acid sequence of Gly-Tyr-Tyr-Pro, all of the constituent amino acids being L-amino acids.

For the dried material of fraction III-3, L-Tyr, L-Gly, L-Gly and L-Trp were successively liberated from the N terminus, which was identified as Peptide F (SEQ ID NO:6) having the amino acid sequence of Tyr-Gly-Gly-Trp, all of the constituent amino acids being L-amino acids.

For the dried material of fraction IV-5, L-Tyr, L-Gly, L-Gly, L-Trp and L-Leu were successively liberated from the N terminus, which was identified as Peptide E (SEQ ID NO:5) having the amino acid sequence of Tyr-Gly-Gly-Trp-Leu, all of the constituent amino acids being L-amino acids.

The yields of Peptides A, B, E and F were determined from the molecular weights and molecular extinction coefficient at Abs. 280, indicating about $4\times10^{-2}$ (%), $4\times10^{-3}$ (%), $1\times10^{-5}$ (%) and $3\times10^{-4}$ (%), successively. The Rf values of Peptides A, B, E and F were determined by thin layer chromatography on silica gel plates using butanol, acetic acid, pyridine, water (15/3/10/12) as a developing solvent, indicating 0.58, 0.54, 0.77 and 0.61, successively.

EXAMPLE 2

Preparation of Peptide Mixture Containing Peptides A, B, E and F from Wheat Gluten Hydrolysates The hydrolysis of wheat gluten was carried out in accordance with the same procedure as in Example 1 except that there was employed as an acid protease the same units of an aspertic proteinase derived from *Aspergillus niger* (available from Yakult Co. under the trade name of "Protease YP-SS") instead of pepsin and the wheat gluten solution adjusted to pH of 3.0 was incubated at 37° C. for 15 hrs. The resulting hydrolysate was subjected to reversed-phase chromatography in a similar manner as in Example 1(2). Opioid activity was found in fractions I, II, III and IV shown in FIG. 1 with the same potency as in Example 1. Thus, there was obtained in this example a peptide mixture with opioid activity containing Peptides A, B, E and F (SEQ ID NOS:1, 2, 5 & 6).

EXAMPLE 3

Preparation of Peptide Mixture Containing Peptides A, B, E and F from Wheat Gluten Hydrolysates The hydrolysis of wheat gluten was carried out in accordance with the same procedure as in Example 1 except that there was employed as a neutral protease the same units of a neutral protease derived from *Aspergillus oryzae* (available from Yamato Chemical Co. under the trade name of "Protin FN") instead of themolysin. The resulting hydrolysate was subjected to reversed-phase chromatography in a similar manner as in Example 1(2). Opioid activity was found in fractions I, II, III and IV shown in FIG. 1 with the same potency as in Example 1. Thus, there was obtained in this example a peptide mixture with opioid activity containing Peptides A, B, E and F (SEQ ID NOS:1, 2, 5 & 6).

EXAMPLE 4

Preparation of Peptide Mixture Containing Peptides A, B, E and F from Wheat Gluten Hydrolysates The hydrolysis of wheat gluten was carried out in accordance with the same procedure as in Example 1 except that there was employed as neutral protease the same units of a cerin protease derived from Bacillus (available from Nagase Sangyo Co. under the trade name of "Bioprase SP-4") instead of themolysin. The resulting hydrolysate was subjected to reversed-phase chromatography in a similar manner as in Example 1(2). Opioid activity was found in fractions I, II, III and IV shown in FIG. 1 with the same potency as in Example 1. Thus, there was obtained in this example a peptide mixture with opioid activity containing Peptides A, B, E and F (SEQ ID NOS:1, 2, 5 & 6).

EXAMPLE 5

Preparation of Peptide D from Wheat Gluten Hydrolysates (1) 5 g of wheat gluten dispersed and dissolved in 100 ml of 0.02 N HCl were centrifuged at 3500 G for 20 minutes to remove an insoluble material and the pH of the solution was adjusted to 2.0 with 1 N HCl. To this wheat gluten solution were added 5000 units of pepsin (available from Sigma Chemical Co., U.S.A.) and the solution was incubated at 37° C. for 15 hrs. After completion of reaction, the pH of the solution was adjusted to 7.0 with 1 N an aqueous NaOH solution, to which were added 5000 units each of trypsin (available from Sigma Chemical Co.) and chymotrypsin (available from Sigma Chemical Co.) and the mixture was incubated at 37° C. for 4 hrs. After completion of reaction, the solution was heated at 90° C. for 20 minutes to deactivate the enzymes. The hydrolysate was centrifuged at 3500 G for 20 minutes to remove an insoluble matter and the resulting supernatant was lyophilized to yield about 3.0 g of a wheat gluten hydrolysate.

(2) The wheat gluten hydrolysate as prepared in (1) was subjected to reversed-phase chromatography (RPC) using an octadecyl silane column, Cosmosil 5 $C_{18}$-AR (20 mm I.D., 250 mm length, Nacalai Tesque Inc.) and then eluted with an aqueous 0.05% trifluoroacetic acid (TFA) solution (solution A) and an acetonitrile (ACN) solution containing 0.05% TFA (solution B) at a flow rate of 10 ml/min with a linear gradient from 0% to 40% solution B over a period of 40 minutes. The chromatogram at a wavelength of 230 nm at that time is shown in FIG. 2.

Figure 2:
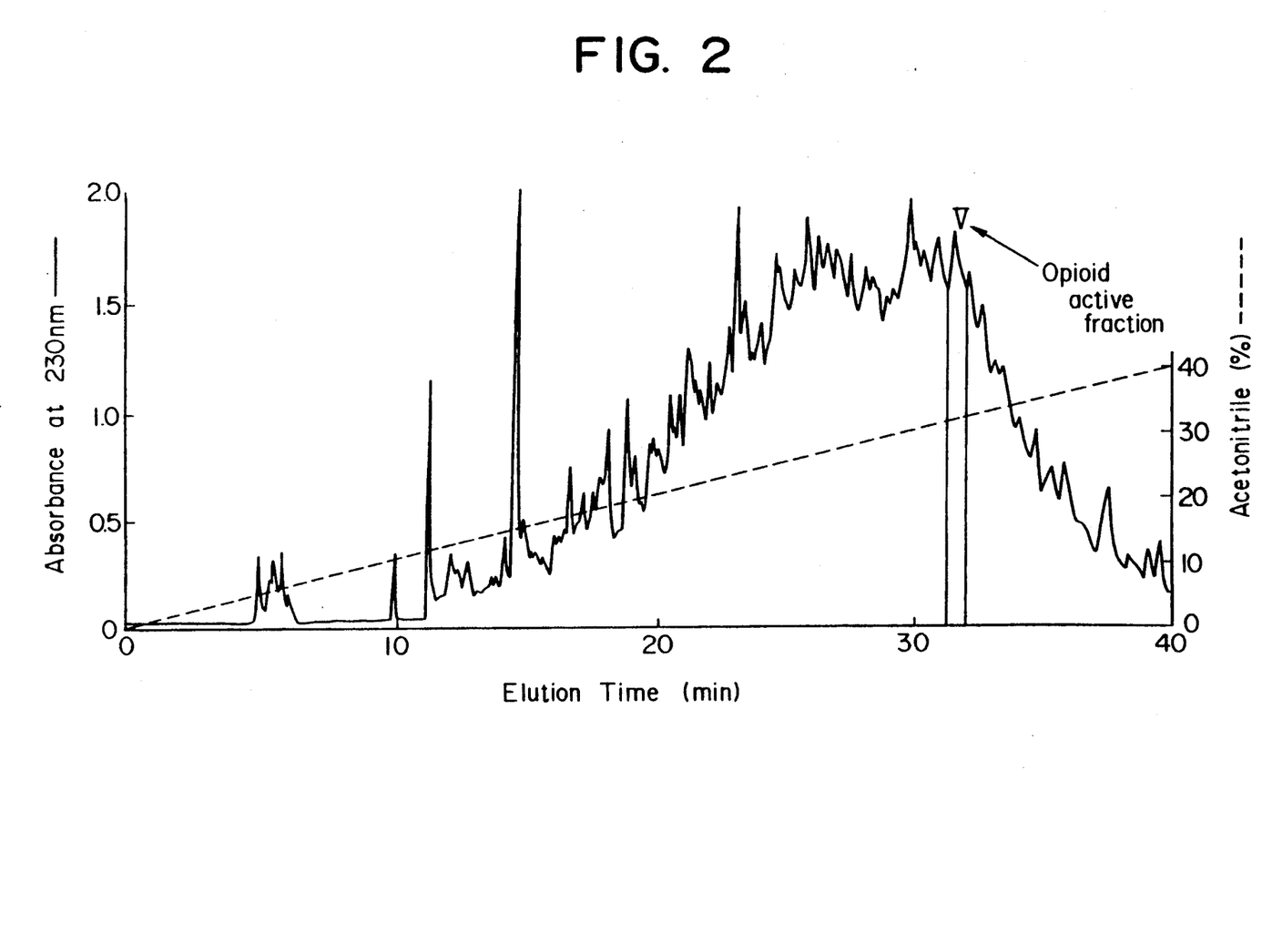
FIG. 2 shows the separation of opioid active fraction V from the ODS column.

The fractions shown in FIG. 2 was determined for opioid activity. Opioid activity was found in fraction V eluting between about 31 and 32% in the ACN concentration.

(3) The same procedure as in (2) was repeated using 2000 mg of the wheat gluten hydrolysate as prepared in (1) to obtain an opioid active fraction of fraction V. This fraction was subjected to RPC on a phenyl column, Cosmosil 5 Ph (4.6 mm I.D., 250 mm length, Nacalai Tesque Inc.) and eluted with solutions A and B at a flow rate of 1 ml/min with a linear gradient from 0% to 40% solution B over a period of 40 minutes.

Each of eluting fractions was determined for opioid activity. Opioid activity was found in fraction V-1 eluting in the ACN concentration of about 33%.

(4) The opioid active fraction in fraction V-1 as prepared in (3) was subjected to RPC on a cyanopropyl column, Cosmosil 5 CN-R (4.6 mm I.D., 250 mm length, Nacalai Tesque Inc.) and eluted under the same conditions as in (3).

Each of eluting fractions was collected and assayed for opioid activity. Opioid activity was found in a peak fraction (fraction V-2) in the ACN concentration of about 27-28%.

(5) The opioid active fraction of fraction V-2 as prepared in (4) above was subjected to reversed-phase chromatography (RPC) on an octadecyl silane (ODS) column, Cosmosil 5 $C_{18}$-AR (4.6 mm I.D., 150 mm length, Nacalai Tesque Inc.) and eluted with 10 mM $KH_2PO_4$—$Na_2HPO_4$ buffer (pH 7) (solution C) and 50% ACN solution containing 10 mM $KH_2PO_4$—$Na_2HPO_4$ buffer (pH 7) (solution D) with a linear gradient from 0 to 100% solution D. Each eluting fraction was collected and assayed for opioid activity.

Opioid activity was found in a high absorption peak fraction (fraction V-3) in the ACN concentration of about 24%.

(6) Fraction V 3 as prepared in (5) was recovered, concentrated and dried.

The dried material as prepared above was investigated for the amino acid sequence using the same model 477-A protein sequencer as used in Example 1. It was found that L-Tyr, L-Pro, L-Ile, L-Ser and L-Leu were successively liberated from the N terminus, which was identified as Peptide D (SEQ ID NO:4) having the amino acid sequence of Tyr-Pro-Ile-Ser-Leu, all of the constituent amino acids being L-amino acids.

The yield of Peptide D from Wheat gluten was determined from the molecular weights and molecular extinction coefficient at Abs. 280, indicating about $4 \times 10^{-4}$ (%). The Rf value of Peptide D was determined by thin layer chromatography on silica gel plates in the same manner as in Example 1, indicating 0.73.

EXAMPLE 6

Preparation of Peptides A-F by Chemical Synthesis (1) Synthesis of Peptide A

A mixture of 0.75 g of a commercially available Boc(-butoxycarbonyl)-Pro-resin (substitution 0.4 meq/g) and 20 ml of methylene chloride containing 45% trifluoroacetic acid and 2.5% anisol was reacted at room temperature for 25 minutes in the reaction vessel of a Sam 2 peptide synthesizer (manufactured by Biosearch Inc.) to remove a Boc group.

The Boc removed-Pro resin was then washed with methylene chloride, neutralized with methylene chloride containing 10% diisopropylethylamine and further washed with methylene chloride.

This resin was mixed with 5 ml of a solution of 0.4 M Boc-Tyr($Cl_2$-Bzl) in dimethylformamide and 5 ml of a solution of 0.4 M diisopropylcarbodiimide in methylene chloride and a mixture was placed into the reaction vessel and reacted at room temperature for 2 hrs. under stirring.

The resultant resin was washed with successive, dimethylformamide, methylene chloride, methylene chloride containing 10% diisopropylethylamine, methylene chloride and methylene chloride/dimethylformamide to obtain a Boc-Tyr($Cl_2$-Bzl)-Pro resin.

Repeated removal of Boc group and coupling of Boc amino acid in the manner as mentioned above gave a product consisting of Boc-Gly-Tyr(Cl -Bzl) Tyr($Cl_2$-Bzl) Pro resin.

This resin was introduced into 20 ml of hydrogen fluoride containing 10% anisol and stirred at 0° C. for 2 hrs to liberate a peptide from the resin.

Subsequently, hydrogen fluoride was distilled off under reduced pressure and the residue was extracted with 30% acetic acid and lyophilized to afford 150 mg of a crude peptide. The crude peptide was purified by reversed-phase chromatography (RPC) using an octadecyl silane (ODS) column (Cosmosil 5 $C_{18}$-AR, Nacalai Tesque Inc.) to obtain 40 mg of a final product with the amino acid composition (molar ratio) of Gly:Tyr:Tyr:Pro = 1:1:1:1. Analysis by the same protein sequencer as used in Example 1 identified the synthesized peptide as Peptide A (SEQ ID NO:1) having the amino acid sequence of Gly-Tyr-Tyr-Pro. Rf value by thin layer chromatography (TLC) was found to be 0.58 as in the product of Example 1.

(2) Synthesis of Peptide B 30 mg of a final product were synthesized from 1 g of a commercially available Boc(butoxycarbonyl)-Thr(Bzl)-resin (substitution 0.3 meq/g) in the same way as mentioned for Peptide A. The amino acid composition (molar ratio) of the product was Gly:Tyr:Tyr:Pro:Thr = 1:1:1:1:1. Analysis by the protein sequencer used in Example 1 identified the synthesized peptide as Peptide B (SEQ ID NO:2) having the amino acid sequence of Gly-Tyr-Tyr-Pro-Thr. Rf value of the product by TLC was found to be 0.54 as in the product of Example 1.

(3) Synthesis of Peptide C 30 mg of a final product were synthesized from 0.77 g of a commercially available Boc-Ser(Bzl)-resin (substitution 0.39 meq/g) in the same way as mentioned for Peptide A. The amino acid composition (molar ratio) was Gly:Tyr:Tyr:Pro:Thr:Ser = 1:1:1:1:1:1. Analysis by the protein sequencer used in Example 1 identified the synthesized peptide as Peptide C (SEQ ID NO:3) having the amino acid sequence of Gly-Tyr-Tyr Pro Thr Ser. Rf value of the product by TLC was found to be 0.53.

(4) Synthesis of Peptide E 40 mg of a final product were synthesized from 0.6 g of a commercially available Boc-Leu-resin (substitution 0.5 meq/g) in the same way as mentioned for Peptide A. The amino acid composition (molar ratio) was Tyr:Gly:Gly:Tyr:Leu = 1:1:1:1:1. Analysis by the protein sequencer used in Example 1 identified the synthesized peptide as Peptide E (SEQ ID NO:5) having the amino acid sequence of Tyr-Gly-Gly-Trp-Leu. Rf value of the product by TLC was found to be 0.77 as in the product of Example 2.

(5) Synthesis of Peptide F 30 mg of a final product were synthesized from 1 g of a commercially available Boc-Trp-resin (substitution 0.3 meq/g) in the same way as mentioned for Peptide A. The amino acid composition (molar ratio) of Peptide E was Tyr:Gly:Gly:Trp = 1:1:1:1. Analysis by the protein sequencer used in Example 1 identified the synthesized peptide as Peptide F (SEQ ID NO:6) having the amino acid sequence of Tyr-Gly-Gly-Trp. Rf value of the product by TLC was found to be 0.61 as in the product of Example 2.

(6) Synthesis of Peptide D 40 mg of a final product were synthesized from 0.6 g of a commercially available Boc-Leu-resin (substitution 0.5 meq/g) in the same way as mentioned for Peptide A. The amino acid composition (molar ratio) was Tyr:Pro:Ile:Scr:Leu = 1:1:1:1:1. Analysis by the protein sequencer used in Example 1 identified the synthesized peptide as Peptide D (SEQ ID NO:4) having the amino acid sequence of Tyr-Pro-Ile-Ser-Leu. Rf value of the product by TLC was found to be 0.73 as in the product of Example 3.

Assay of Opioid Activity

Two mouse vas deferens excised from male ICR mice weighing 30-35 g were connected to an isotonic transducer (TB 612-T, Nippon Koden Kogyo Inc., Japan) with 0.4 g tension. Each of the mouse vas deferens was immersed in a 2 ml magnus tube maintained at 36° C. in which Krebs solution was filled comprising 118 mM NaCl, 4.75 mM KCl, 2.54 mM $CaCl_2$, 25 mM $NaHCO_3$, 1.19 mM $KH_2PO_4$ and 11 mM glucose and ventilation (95% $O_2$, 5% $CO_2$) was performed from bomb. After stabilization for about 2 hrs in this manner, electrical stimulation (30 V, 1 msec) was applied to the mouse vas deferens for electrical contraction. After electrical contraction was stabilized, 50 μl of an inhibitor (containing an amino peptidase inhibitor, etc.) were added to the contents of the magnus tube. Then each fraction separated from wheat gluten hydrolysates by high performance liquid chromatography was added to the tube and the change in electrical contraction of the mouse vas deferens was recorded. Opioid activity was judged from inhibition of the electrical contraction after addition of each fraction and reverse of the inhibition by addition of 20 μl of $10^{-4}$ M naloxone. Each fraction was determined for the concentration ($IC_{50}$) which inhibits the electrically stimulated contraction of the mouse vas deferens by 50%.

$IC_{50}$ values of Peptides A-D are shown in Table 1.

TABLE 1

| Peptide | $IC_{50}$ (μM) |
|---------|----------------|
| Peptide A | 70 |
| Peptide B | 40 |
| Peptide C | 75 |
| Peptide D | 15 |

What is claimed is:

1. An opioid peptide selected from the amino acid sequence group consisting of:

| | |
|---|---|
| Gly—Tyr—Tyr—Pro | (SEQ ID No: 1) |
| Gly—Tyr—Tyr—Pro—Thr, | (SEQ ID No. 2) |
| Gly—Tyr—Tyr—Pro—Thr—Ser and | (SEQ ID No: 3) |
| Tyr—Pro—Ile—Ser—Leu. | (SEQ ID No: 4). |

2. A pharmaceutical composition comprising at least one opioid peptide of claim 1 or a physiologically acceptable salt thereof in a pharmaceutically acceptable carrier.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Gly Tyr Tyr Pro
1

( 2 ) INFORMATION FOR SEQ ID NO:2:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Gly Tyr Tyr Pro Thr
1               5

( 2 ) INFORMATION FOR SEQ ID NO:3:

( i ) SEQUENCE CHARACTERISTICS:
( A ) LENGTH: 6 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Gly Tyr Tyr Pro Thr Ser
1               5

( 2 ) INFORMATION FOR SEQ ID NO:4:

( i ) SEQUENCE CHARACTERISTICS:
( A ) LENGTH: 5 amino acids
( B ) TYPE: amino acid
( D ) TOPOLOGY: linear ( i i ) MOLECULE TYPE: peptide ( x i ) SEQUENCE DESCRIPTION: SEQ ID NO:4:

Tyr Pro Ile Ser Leu
1               5

( 2 ) INFORMATION FOR SEQ ID NO:5:

(i) SEQUENCE CHARACTERISTICS:
   (A) LENGTH: 5 amino acids
   (B) TYPE: amino acid
   (D) TOPOLOGY: linear (ii) MOLECULE TYPE: peptide (xi) SEQUENCE DESCRIPTION: SEQ ID NO:5:

Tyr Gly Gly Trp Leu
1               5

(2) INFORMATION FOR SEQ ID NO:6:

(i) SEQUENCE CHARACTERISTICS:
   (A) LENGTH: 4 amino acids
   (B) TYPE: amino acid
   (D) TOPOLOGY: linear (ii) MOLECULE TYPE: peptide (xi) SEQUENCE DESCRIPTION: SEQ ID NO:6:

Tyr Gly Gly Trp
1